United States Patent
Gohlke et al.

(10) Patent No.: US 6,780,438 B2
(45) Date of Patent: *Aug. 24, 2004

(54) DIETARY SUPPLEMENT COMPRISING COLOSTRUM AND CITRUS PECTIN

(75) Inventors: Marcus B. Gohlke, Houston, TX (US); Richard H. Cockrum, Perry, IA (US)

(73) Assignee: Lactoferrin Products Company, Houston, TX (US)

( * ) Notice: Subject to any disclaimer, the term of this patent is extended or adjusted under 35 U.S.C. 154(b) by 91 days.

This patent is subject to a terminal disclaimer.

(21) Appl. No.: 10/209,546

(22) Filed: Jul. 31, 2002

(65) Prior Publication Data

US 2002/0187200 A1 Dec. 12, 2002

Related U.S. Application Data

(62) Division of application No. 09/945,997, filed on Sep. 4, 2001, now Pat. No. 6,475,511, which is a division of application No. 09/778,294, filed on Feb. 6, 2001, now Pat. No. 6,410,058, which is a division of application No. 09/370,654, filed on Aug. 6, 1999, now Pat. No. 6,258,383.

(60) Provisional application No. 60/096,697, filed on Aug. 14, 1998.

(51) Int. Cl.$^7$ ................................................. A61K 35/78
(52) U.S. Cl. ........................ 424/535; 424/440; 424/441; 424/464; 424/736
(58) Field of Search ................................ 424/535, 440, 424/441, 464, 736

(56) References Cited

U.S. PATENT DOCUMENTS 6,258,383 B1 * 7/2001 Gohlke et al.

* cited by examiner

Primary Examiner—Francisco Prats
Assistant Examiner—Susan D. Coe
(74) Attorney, Agent, or Firm—Howrey Simon Arnold & White

(57) ABSTRACT

A dietary supplement for mammalian consumption, and particularly human consumption, for the purpose of stimulating the immune system, inhibiting infection and increasing tissue repair and healing. Comprising colostrum, lactoferrin, and with modified citrus pectin as an optional component, the dietary supplement is administered in 'mucosal delivery format': a dosage form that promotes effective absorption through the lining of the oral cavity.

5 Claims, No Drawings

DIETARY SUPPLEMENT COMPRISING COLOSTRUM AND CITRUS PECTIN

CROSS REFERENCE TO RELATED APPLICATIONS

This is a divisional application of U.S. patent application Ser. No. 09/945,997 now U.S. Pat. No. 6,475,511, filed Sep. 4, 2001, which was a divisional application of U.S. patent application Ser. No. 09/778,294 (now U.S. Pat. No. 6,410,058), filed Feb. 6, 2001, which was a divisional application of U.S. patent application Ser. No. 09/370,654 (now U.S. Pat. No. 6,258,383), filed Aug. 6, 1999, which was a non-provisional application of U.S. Patent Application Ser. No. 60/096,697, filed Aug. 14, 1998.

BACKGROUND OF THE INVENTION

1. Field of the Invention

This invention relates to the field of natural dietary supplements. It relates particularly to dietary supplements that are able to aid the prevention or inhibition of infection, promote immunological stimulation or increase tissue repair or healing. It is directed particularly towards the supplementation of human diets, and provides for enhanced absorption of the proteinaceous active ingredients in the oral cavity.

2. Background of the Invention

Nutrition is a critical determinant of immunological competence and of the individual's ability to resist infection and physiological stresses. The health of individuals is affected by poor decisions in society's management of new technology over the past five decades. In particular, the routine use of antibiotics, the consumption of processed foods and the pollution of the environment have resulted in multiple adverse influences upon health. Among these may be included the proliferation of new strains of bacteria and viruses that are resistant to existing antibiotic and antiviral agents, compromised immune systems resulting from chemical pollutants in food, water and air, as well as impaired ability to repair tissue and muscle. Additionally, emotional and physical stresses from employment, family, exercise and the natural effects of aging reduce the effectiveness of the immune system and tissue repair processes.

The continuing widespread use of antibiotics in medicine and agriculture reinforces the selective pressures that increase the types and extent of antibiotic-resistant microbes in the environment, which then substantially increases the cost of treating infection. Moreover, administration of antibiotics frequently causes disruption of the normal bacterial flora colonizing the individual's digestive tract, with results that are particularly undesirable in weakened patients.

The physiological rigors to which an individual's body is exposed in the modern environment, which include the chemical pollutants and antibiotic-resistant microbes discussed above, indicate the advisability of boosting the immune system to facilitate the body's abilities to resist and cope with infection, and to assist the natural, self-healing processes. Two groups of individuals are particularly susceptible to infection and the side effects of treatment: young children and the aged. These individuals may respond poorly to physiological or environmental challenges because they typically possess immune systems that are, in young children and in the aged respectively, immature or damaged. Consequently, natural stimulation of these individuals' immune systems is particularly desirable.

3. Description of the Prior Art

Stimulation of the immune system may occur if the appropriate proteins are absorbed into an individual's bloodstream. Yet these proteins are not only degraded rapidly by the acidic and enzymatic conditions of the stomach and intestine but they are also expensive to obtain, even in the quantities and formats used for experimental demonstrations: Lönnerdal & Iyer, 1995, *Annu. Rev. Nutr.*, 15: 93–110. Thus attempts to formulate an effective dietary supplement able to generate and maintain a state of immune stimulation in an individual have been unsuccessful.

If the components of a dietary supplement were to possess, in addition to nutritional characteristics, abilities that aid the body's capacity to resist fresh infection, to suppress existing infection or to increase tissue repair and healing, such abilities would naturally prove advantageous for achieving the general health enhancing purposes outlined above. As indicated below, those skilled in the art of the respective fields recognize that each of the two proteinaceous products colostrum and lactoferrin is able to perform beneficial activities of this type: see, for example, Wang, et al., 1995, *J. Leuk. Biol.*, 75: 865–874, and Burrin et al., 1995, *Pediatr. Res.*, 37: 593–599.

Colostrum is the pre-milk produced immediately after birth before the breast secretions stabilize into milk. Prime colostrum from cows is obtained within the first six hours after calving and contains more than twice the milk solids and four times the protein found in milk from the same cow obtained forty-eight hours later. The concentrations of digestive enzymes, immunoglobulins, cytokines, interferons, glycoproteins, proline-rich peptides and vitamins A, D, E and K are all higher in prime colostrum than in the later breast secretions. The immunoglobulin fraction of the prime colostrum provides the newborn with antibodies, lactoferrin and immune enhancers. These components offer the newborn protection against viruses, bacteria, allergens and toxins, assisting desirable Acidophilus bacteria to start the colonization of the newborn's intestine and help prevent the development of gastrointestinal infection. Proline-rich peptides (e.g. colostrinin) are immunomodulatory peptide components of colostrum: Janusz and Lisowski, 1993, *Arch. Immunol. Therap. Experiment.*, 41: 275–279. These proline-rich peptides are regulators of the thymus gland, which in turn produces T-lymphocytes that neutralize antigens, including infectious agents such as bacteria and viruses. Colostrum also contains a combination of growth factors that combat disease, reduce infection and enable the newborn to grow healthily and to heal rapidly: see, for example, Oda et al., 1989, *Comp. Biochem. Physiol.*, 94A: 805–808 and Xu et al., 1994, *Biol. Neonate*, 66: 280–287. That even healthy adults may benefit from the administration of colostrum is suggested by studies showing that bovine colostrum whey increases serum levels of insulin-like growth factor (IGF-I) in athletes undergoing training: Mero et al., 1997, *J. Appl. Physiol.*, 1997, 83: 1144–1151. Colostrum balances blood sugars during periods of hyperglycemia or hypoglycemia, slows catabolism and the breakdown of muscle protein, and it stimulates fat utilization.

In sum, prime colostrum contains powerful healing, growth and repair factors that activate numerous immune, healing, growth and repair systems and assist in synthesis, retention and repair of muscle, bone, nerve and cartilage. As the body ages, becomes weakened by illness, or is subjected to physical stresses, it produces less and less of the growth, healing and repair factors that are needed to overcome illness and to heal quickly.

Ettinger, U.S. Pat. No. 4,762,822 (expired) describes the use of human colostrum as a source for extracting ganglioside, with human milk or mammalian brain being alternative sources. As one of several alternative components of young mammals' dietary supplements the extracted ganglioside is used to improve mother's milk substitute foods or for reducing the numbers of gastrointestinal disease-producing organisms in a young mammal.

Lactoferrin is a protein that is secreted in milk, tears, mucus and saliva, and is expressed by white cells at the site of attack by numerous pathogens. A primary function of lactoferrin is to bind iron at the molecular level and thereby act as a highly effective antimicrobial agent. Iron is an essential growth factor for virtually every cell and microorganism, and free iron promotes the growth of pathogens in the intestines (bacteria, viruses and fungi), permitting invasion of the rest of the body through the intestinal walls: Gillon Ward et al., 1996, *J. Trauma, Inj. Inf. Critical Care,* 41: 356–364. Lactoferrin is released by cells to absorb free iron that would otherwise be available to bacteria, viruses and fungi for growth. Unlike synthetic antibiotics, to which bacteria may develop resistance through mutation, lactoferrin exerts its bacteriostatic effect as long as the bacteria require iron for growth.

Additionally, lactoferrin is recognized by specific receptors in mammalian tissues to release iron to the body for normal, healthy cell growth. Unlike synthetic antibiotics, lactoferrin has the ability to bind iron, transport it and then release the iron specifically to the body's own cells through cell surface lactoferrin receptors.

Lactoferrin is a multifunctional protein that is expressed in a variety of cell types under different mechanisms of control. It has been demonstrated that lactoferrin plays a central role in the inflammatory defense processes. Released in abundant quantities by neutrophils attracted to the site of an invasion, lactoferrin binds the iron made available by serum and damaged erythrocytes. Monocytes and macrophages ingest the iron-saturated lactoferrin, which has also been implicated in the production of metastable oxygen metabolites associated with bacterial destruction within these blood cells: Wang, et al., 1995, *J. Leuk. Biol.,* 75: 865–874. Lactoferrin also regulates the release of tumor necrosis factor alpha (TNF-α) and interleukin 6 (IL-6) in vivo: Machniki et al, 1993, *Int. J. Exp. Path.* 74: 433–439.

Due to the iron absorption and release functions of this protein, lactoferrin is the body's primary regulator of iron, a major bio-regulator of the digestive tract and a natural bacteriostatic agent having indirect but broad antibiotic effects. Yet the cost and availability of human lactoferrin, purified from human breast milk, restricts its use to research.

Lactoferrin's iron-binding bacteriostatic effect, coupled with its general abundance in breast milk, has led to numerous studies in new-born mammalian offspring, prompting its incorporation into Japanese baby formula since approximately 1993. Lactoferrin B is an amino terminal peptide of bovine lactoferrin generated by pepsin digestion and has been shown to have a potent bacteriocidal activity against a diverse range of potentially pathogenic bacteria: Bellamy et al., 1992, *J. Applied Bacteriol.,* 73: 472–479. The importance of lactoferrin in newborn humans for ensuring the appropriate formation and development of the gastrointestinal tract, its bacterial colonization and to enable nutrients to be absorbed effectively, has also been demonstrated.

Many of these functions of lactoferrin are reviewed by Lönnerdal & Iyer, 1995, *Annu. Rev. Nutr.,* 15: 93–110. Yet these authors note that the relative efficacy of using either lactoferrin from other species, or recombinant human lactoferrin for treatment of humans is unproven. This is because adequate quantities of human lactoferrin have not been isolated to supply clinical studies, and recombinant human lactoferrin will not accurately reproduce the protein's glycan composition.

Tanaka et al, U.S. Pat. Nos. 5,098,722 and 5,008,120 disclose methods of preparing iron-fortified beverages that contain a solution of purified bovine lactoferrin and provide high bio-availability of iron.

Tomita et al., U.S. Pat. No. 5,304,633 disclose fragments of milk lactoferrin having potent antimicrobial activity. Kunio et al., U.S. Pat. No. 5,576,299 disclose the use of lactoferrin for preventing and treating the opportunistic infections that arise in immuno-compromised individuals. Yamamoto et al., U.S. Pat. No. 5,725,864 disclose the use of an iron-binding protein, of which lactoferrin is one of several examples, for inhibiting infection or suppressing growth of human immunodeficiency virus: the protein is administered by diffusion through any of several epithelial membranes, or by injection. Valenti & Antonini, U.S. Pat. No. 5,834,424 disclose the use of compositions containing lactoferrin or other iron-binding proteins for treating Gram-positive bacterial infections.

Nichols & McKee, U.S. Pat. No. 4,977,137 describe the use of milk lactoferrin from human and other mammalian sources as a dietary ingredient or supplement. The lactoferrin promoted growth of the gastrointestinal tract of human infants or non-human animals immediately on birth. Konig et al., U.S. Pat. No. 5,466,669 disclose an immunostimulatory agent comprising a peptide derived from lactoferrin.

Headon et al., 1990, PCT/US90/02356, European Patent No. 0 471 011 B1, disclose the verified cDNA sequence of human lactoferrin. Kruzel, 1991, PCT/US91/01335 discloses human lactoferrin expressed from recombinant DNA, its method of production and purification and its use for supplementing the diet with trace elements or as a topical antiseptic. Kruzel et al., 1995, PCT/US95/05653 disclose the cloning, expression and uses of recombinant human lactoferrin for retarding food spoilage, as a topical antiseptic, for inhibiting microbial growth in or on a mammal, for regulating iron levels within a mammal or for a nutritional supplement.

Citrus pectin obtained from citrus peel is modified by a standard technique involving limited proteolysis, facilitating passage into the bloodstream of the smaller polypeptide products. Galactose residues located on the surface of both the original pectin glycoprotein and the more soluble polypeptide products bind lectins, including cell surface proteins of some cancer cells: Raloff, 1995, *Science News,* 14: 134. Modified citrus pectin consumed in drinking water has been shown to halt the spread of prostate cancer cells: Pienta et al., 1995, *J. Nat'l. Cancer Inst.,* 87: 348–353.

See, U.S. Pat. No. 5,747,464 discloses the use of apple pectin bound irreversibly to β-sitosterol in a composition which is used as a dietary supplement for inhibiting absorption of fat and cholesterol from the gut.

The strongly acidic conditions of the stomach, and the function of the proteolytic enzymes and zymogens produced in the pancreas and acting in the intestines, are well known to inactivate and degrade the delicate structures of proteins, such as the components of the dietary supplements described here. As reviewed by Lönnerdal & Iyer, 1995, *Annu. Rev. Nutr.,* 15: 93–110, the species-specific glycosylation of lactoferrins from different mammalian sources may provide protection from proteolysis for lactoferrin ingested naturally from maternal milk, and cross-species administration of lactoferrin would be expected to be far less effective. Even if the lactoferrin succeeds in reaching the small intestine intact, specific lactoferrin receptors enable human lactoferrin to deliver iron to the mucosal cells of human small intestine, whereas bovine lactoferrin is incapable of doing so: Cox et al., 1979, *Biochim. Biophys. Acta,* 558: 129–141.

In spite of the knowledge of the beneficial properties of either colostrum or lactoferrin when used individually, there remains a continuing need for an economical dietary supplement to boost the body's own defense and repair systems and to provide for increased energy, stamina, resilience and tissue repair. The components of the supplement must be obtainable from economic and abundant sources, yet remain effective for administration to humans, and preferably to a broad range of recipient mammals. Moreover, such a dietary supplement must be absorbed effectively, without the degradation of protein constituents that is associated with regular digestive processes such as the destruction of delicate immunoglobulins by acids in the stomach.

The oral cavity contains a plethora of mechanisms to counter the survival of infectious agents that enter through the mouth and nose: secreted with the saliva are broad-spectrum IgA antibodies, lysozymne and small quantities of lactoferrin, and lymphoid cells enter the oral cavity through the gingiva. In addition, it has recently been recognized that external factors may also deliver signals that modulate immune responses: these factors include cytokines such as the interferons, as well as hormones, growth factors and cellular antigens.

Studies aimed at preventing allergic inflammation in rodents have indicated that administration of interferon to mice by oral feeding could be as effective as intraperitoneal injection. Thus oral administration of either antigens or cytokines may be capable of modulating a variety of physiological reactions, including immune responses. Possible routes of mediation are: (a) taste buds of the tongue, connected by nerves to hypothalamus collateral centres, control appetite and energy utilization; (b) a spectrum of mucosal and secretory cell types present in the oral cavity that are capable of responding to cytokine or antigen signals and releasing further cytokine messages; (c) epithelial cells of the oral cavity, which are likely to be the natural recipients of signals entering the mammalian mouth: in the adult these would be primarily signals from antigens, whereas for the neonatal mammal important signals would also be received from ingested maternal cytokines and maternal hormones; (d) the submucosal tissue of the oral cavity, which secretes immunoglobulin IgA. Small amounts of either cytokine or antigen may be recognized as antigen by a responsive cell, resulting in immune activation via initiation of the cytokine cascade, whereas large doses or extended administration may induce tolerance: studies have shown that interferon administered in large doses to humans may be less effective than minimal quantities. Thus the response will frequently be individual or case dependent and may be strongly influenced by additional physiological or environmental factors.

The implications of these immunological studies have been reviewed recently (Georgiades, 1998, *Biotherapy*, 11: 39–51) with the conclusion that the tolerance phenomenon is not only limited to the oral administration of antigen but may occur when immunization is attempted via any mucosal membrane, such as the nasal tract. In the light of such conflicting results and controversial hypotheses it could be considered counter-intuitive, and certainly unpredictable, to attempt to stimulate or potentiate an immune response by administering cytokinins and immunoglobins orally by means of a combination of prime colostrum and lactoferrin.

4. Objects of the Invention

The invention addresses the requirement for an effective and economical dietary supplement comprising one or more natural stimulators of immune function, prevention of and protection from infection, and improved tissue repair and healing. Furthermore, this supplement must be provided in a convenient format that permits absorption of the active components into an individual's bloodstream in a manner that avoids the body's normal digestive mechanisms. The present invention emphasizes the efficacy of oral administration of the dietary supplement and promotion of the supplement's efficient absorption through the oral cavity's epithelial lining by presenting the supplement in a 'mucosal delivery format' (MDF). Those MDFs of the invention that are preferred, e.g. chewable lozenges, also render the dietary supplement of the invention particularly adaptable to self-monitored dosages, and are especially appropriate for regimes of self administration.

SUMMARY OF THE INVENTION

The present invention encompasses dietary supplements containing lactoferrin and colostrum in combination, thus providing an improvement over previous supplements which lacked one or other or both of these components. When absorbed in combination the effects of colostrum and lactoferrin on the health and well-being of the recipient are surprisingly beneficial, being greater than would be anticipated from the known properties of each component taken in isolation and including the promotion of resistance to infection, stimulation of immune function and the increase of tissue repair and healing. Absorption of the components in the oral cavity, rather than through the lining of either the stomach or intestine is particularly efficacious: hence the invention includes the provision of the components in a mucosal delivery format, or 'MDF', such as a chewable lozenge.

The present invention provides a dietary supplement containing lactoferrin and colostrum, which may also contain modified citrus pectin. It also provides a composition containing these ingredients which may also include nutritionally acceptable carriers, diluents and flavorings, a method of administering such a composition in a form appropriate for absorption through the lining of the oral cavity, and a method of promoting resistance to infection, stimulation of immune function and an increase of tissue repair and healing.

Thus a mucosal delivery format that combines lactoferrin with prime colostrum boosts the body's defense, growth, healing and repair systems, enhances immune system function, and binds excess free iron. This results in increased energy and stamina, accelerated tissue repair and improved resilience to infection. Providing the dietary supplement in the form of lozenges which may be dissolved slowly in the mouth permits the lactoferrin and colostrum to achieve their optimal effects: to energize the immune system to build the body's own disease defenses naturally, to keep pathogens in check and to help the body repair vital tissue. The inclusion of modified citrus pectin as a component of the dietary supplement offers the potential for providing protection from the spread of certain cancers. Taking one of the lozenges of the invention once or twice or more often per day, as needed, provides the suggested dietary supplement. Immuno-compromised individuals, diabetics (particularly 'brittle diabetics') and the elderly can benefit from larger doses of lozenges.

DETAILED DESCRIPTION OF THE INVENTION

The invention has been found effective for numerous physiological disorders caused by and resulting in a variety of metabolic insults, including routine antibiotic use, toxic pollutants, processed foods, stress, aging and impaired muscle repair.

The invention encompasses compositions, dietary supplements and methods for their use that include the following active components:

(a) Prime colostrum has the highest concentrations of immunoglobulins, interferons, proline-rich peptides, amino acids and vital enzymes produced by mammary tissue, being higher than those produced in ordinary colostrum. This provides the newborn with protection against viruses and bacteria and other health threats. Besides providing the first complete food for the newborn, prime colostrum has profound immuno-stimulating properties: administration of very small amounts activates the human immune system. In addition to this immune stimulation capability, prime colostrum provides immunoglobulins directly (e.g. IgA, IgG, IgM) and also growth factors (e.g. IGF-I, TGF A and B). It supplies immunomodulatory proline-rich peptides which moderate the activity of the immune system through their effect upon the thymus gland, stimulating under-active immune systems such as those of immuno-compromised persons, or moderating those that are over-active as in individuals with auto-immune diseases. Prime colostrum slows muscle breakdown, improves protein synthesis and utilization, provides digestive enzymes, regulates blood sugar and stimulates growth and repair. In sum, prime colostrum contains powerful healing, growth and repair factors that activate numerous immune, healing, growth and repair systems and assist in synthesis, retention and repair of muscle, bone, nerve and cartilage. As the body ages, becomes weakened by illness, or is subjected to physical stresses, it produces less and less of the factors that are needed to overcome metabolic insults or infection and to heal quickly.

(b) Lactoferrin is an iron binding protein that occurs naturally in the body. It is secreted in milk, tears and saliva, and is expressed by white blood cells. Lactoferrin is well known in the art as a biological regulator that performs many important functions in the body. These functions include maintaining a healthy balance in the digestive tract, helping the immune system and promoting healthy cell growth. Dairy cattle currently provide the only cost-effective source of lactoferrin for inclusion into a dietary supplement, even though cows' milk contains a relatively low concentration of to lactoferrin. Lactoferrin from cows' milk can be prepared free of lactose; it bioregulates iron, boosts the immune system, balances the digestive tract, increases energy and stamina and promotes cell growth and healing. These broad, beneficial properties are surprising in view of the inability of bovine lactoferrin to bind to the lactoferrin receptors at the surface of the mucosal cells of human small intestine.

(c) Modified citrus pectin is an optional component that endows the composition with additional benefits as a nutritional supplement. Citrus pectin is a protein that contains galactose molecules on its surface which are able to bind lectins involved in the transmission within the body of certain types of cancer. Modified citrus pectin has been treated to reduce its molecular size, thereby increasing its solubility and ability to be absorbed into the bloodstream.

(d) Citric acid is a further optional component that may be incorporated to promote salivation and to adjust the acidity of the composition in order that solubility, activity and absorption of the components within the oral cavity is enhanced.

Iron is a key mineral required by all microorganisms for maintenance and growth. Excess iron in the intestines promotes pathogen growth and proliferation. Lactoferrin from cows' milk is partially saturated with iron (approximately 25% of total saturation) providing a dietary source of iron as well as a means of scavenging free iron from the oral cavity and digestive tract. Lactoferrin works on contact to starve pathogens of iron so that the correct balance of beneficial bacteria develops and is maintained in the digestive tract; the growth of harmful bacteria that are poorly adapted to these conditions being inhibited. By sequestering iron and delivering it for use by the cells of the body's internal tissues lactoferrin improves digestion and boosts the body's natural defense mechanisms. This generates more energy and increased stamina for physical activities and optimum health.

Lactoferrin and prime colostrum achieve their optimal effects when dissolved slowly in the mouth, rather than being swallowed directly in the form of a pill or capsule. Slowly dissolving the lactoferrin and constituents of colostrum in the mouth permits their absorption into the capillaries at the surface of the oral cavity's lining, and this is able to occur before the lactoferrin and prime colostrum are exposed to the harsh degradatory conditions of the stomach and intestines. For example, bovine lactoferrin is less resistant to degradation in the human digestive tract than is human lactoferrin, and the lactoferrin receptors in the small intestine of humans will not bind bovine lactoferrin. Thus administration of bovine lactoferrin to humans in a mucosal delivery format, such as a format that enables its absorption through the lining of the mouth, is particularly efficacious. Inmunoglobulins from colostrum also pass directly into the blood through the inner mucosal layer of the mouth. Prime colostrum is capable of energizing the immune system when the appropriate dose is slowly absorbed by the body: as little as 125 mg of prime colostrum in the oral cavity will trigger an immune response event. Orally delivered prime colostrum stimulates the body to replace growth, healing and repair factors as needed and produce them naturally to achieve homeostasis. Oral administration of modified citrus pectin has been shown to be effective for inhibiting spontaneous metastasis of a rat prostate cancer.

Lozenges, in contrast to pills or capsules, provide a 'mucosal delivery format' (MDF) for constituents which can be absorbed through the oral mucosal surface, such as the colostrum, lactoferrin or modified citrus pectin of the invention. In particular, the lozenges of the invention are able to enhance the benefits associated with absorption of appropriate constituents through the oral epithelial mucosa and into the under-lying lymphatic system, for they are designed to be dissolved slowly in the mouth and they may also be chewable: such lozenges are therefore a preferred MDF. By using a cold-pressing technique to manufacture the lozenges heat degradation of sensitive biological components is minimized. Lozenges are also preferable to hard-pressed tablets or capsules for the latter do not dissolve until exposed to the gastric juices of the stomach. These strongly acidic juices degrade the interferon, the other immuno-stimulating proteins and immunoglobulins that are contained in colostrum. Similarly, oral administration using lozenges as the mucosal delivery format, but not capsules or hard tablets, allows the lactoferrin to sequester iron in the upper digestive tract and thereby broaden the effect of its bacteriostatic actions.

The present invention, in common with many dietary supplements, incorporates ingredients derived from dairy sources. Dairy products generally contain sufficient lactose to prevent lactose-intolerant individuals from using them in their diets. Ingestion of 77 mg lactose can be sufficient to create an adverse response in a lactose-intolerant individual. The present invention uses highly purified products, including lactose-free lactoferrin and prime colostrum that contains no more than 10% lactose. This enables lactose levels to be maintained at or below 75 mg lactose per individual dosage so that adverse responses will be avoided while incorporating prime colostrum at up to 750 mg. Also, the use of prime colostrum itself provides an advantage in this regard, as its ratio of beneficial protein to lactose is greater than in regular colostrum.

In its first feeding, a new-born calf ingests prime colostrum, which itself contains lactoferrin. However, the proportion of these ingredients is very different to that in the dietary supplement of the invention. The initial one-half liter liquid colostrum provided by a cow provides 110 g dry weight prime colostrum, including 55 mg lactoferrin (a ratio of 2000:1). As described in the Examples, the typical dosage unit of the invention provides 150 mg prime colostrum and 10 mg lactoferrin (a ratio of 15:1), delivered to a mammal of comparable size. Yet the beneficial effects of the invention are observed in spite of these ingredients being delivered in far smaller quantities (several orders of magnitude in the case of the colostrum component). Thus the invention serves as a true dietary supplement, requiring combination of the ingredients in an unpredictable proportion.

Given the species-specificity of human intestinal lactoferrin receptors and the apparent ease with which antigenic tolerance can be induced in a variety of mammals from rodents to primates, the efficacy of the invention in achieving its stated aims is remarkable. By administering the combination of bovine prime colostrum and bovine lactoferrin not only are beneficial effects of each component observed, but a synergistic effect is apparent: the results of combined administration are greater than may be accounted for by an additive effect of the individual components. The results observed, and described below in the Examples, may stem not only from the novel combination of ingredients, but also from the manner in which they are administered and the apparent inducement of immunological responses that is possible when such materials are provided in the recommended doses and allowed to be absorbed through the epithelial lining of the oral cavity.

The individual components of the composition may be obtained from commercial sources: colostrum (which is dehydrated by standard spray-drying procedures known in the art) from any processing facility approved by the U.S. Food and Drug Authority (F.D.A.) such as Immuno-Dynamics, Inc. of Perry Iowa, U.S.A.; lactoferrin from approved manufacturers such as DMV International Nutritionals of Frazier N.Y., U.S.A.; modified citrus pectin from approved distributors or manufacturers such as G.C.I. of Los Angeles Calif., U.S.A.; flavors from approved distributors or manufacturers such as Allen Flavors, Inc. of Edison N.J., U.S.A. Manufacturing of the composition, the dietary supplement, and the oral dosage forms may each be performed using standard techniques appropriate for the food or pharmaceutical industries, as at F.D.A. approved facilities such as Summa Rx Laboratories, Inc. of Mineral Wells Tex., U.S.A.

1. Description of Presently Preferred Embodiments

A preferred embodiment of the invention is a composition for use as a dietary supplement for a mammal, comprising nutritionally effective amounts of colostrum and of the protein lactoferrin, sufficient to promote an effect in the mammal that is selected from: resistance to fresh infection, suppression of existing infection, stimulation of immune function, and the increase of tissue repair and healing. A particularly preferred embodiment is such a composition for use as a dietary supplement for humans.

Preferred embodiments of the invention comprise such a composition in which the lactoferrin is present at a concentration of from about 10 mg to about 100 mg per 1500 mg total weight and the colostrum is dehydrated colostrum, prepared by a mechanism such as spray drying, and present at a concentration of from about 125 mg to about 1250 mg per 1500 mg total weight. In such a preferred embodiment a 1500 mg dose is typically provided from one to about five times per day. Supplementary doses may be warranted under particular nutritional or physiological conditions. Additional preferred embodiments include such compositions for use as a dietary supplement that additionally comprise modified citrus pectin at a concentration of from about 1.5 mg to about 15 mg per dose.

Further preferred embodiments include such compositions, with or without modified citrus pectin, in which the lactoferrin is obtained from milk, particularly bovine milk, and also where the colostrum is prime colostrum, especially that from bovine sources. In any of these embodiments the composition may further comprise nutritionally acceptable carriers, adjuvants or diluents as are known in the art. Advantages of incorporating such additional components include stabilization of the composition for easier or more effective preparation, distribution or administration, improvement of the effectiveness of delivering the active components once administered and, as described below for fillers, sweeteners and flavors, to increase the attractiveness of the composition as an edible product.

Another preferred embodiment of the invention is a dietary supplement for promoting in mammals, especially humans, an effect of resistance to fresh infection, suppressing existing infection, stimulating immune function, or increasing tissue repair and healing; wherein the dietary supplement comprises the composition that includes nutritionally effective amounts of colostrum and of the protein lactoferrin and may additionally include modified citrus pectin. Preferred sources, types, methods of preparation and concentration ranges for these components are as indicated above. The dietary supplement is preferably prepared in a 'mucosal delivery format'; particularly as an oral dosage form that promotes absorption of the dietary supplement's components within the oral cavity. Such forms are described in greater detail below.

An additional preferred embodiment of the invention is a method of promoting in mammals an effect of resistance to fresh infection, suppressing existing infection, stimulating immune function, or increasing tissue repair and healing: the method comprises the administration of an effective amount of dietary supplement containing the composition that includes nutritionally effective amounts of colostrum and of the protein lactoferrin. The composition may additionally include modified citrus pectin. An especially preferred embodiment is that in which the mammal is human. Preferred embodiments include methods in which the sources, types, methods of preparation and concentration ranges of the components of the composition are as described above. Other preferred embodiments include those in which the dietary supplement is prepared in a 'mucosal delivery format'; particularly as an oral dosage form to promote absorption in the oral cavity, as indicated above.

Further preferred embodiments of the invention include compositions, dietary supplements and methods, as described above, in which the composition contains one or more of the following components: citric acid, dextrose and/or sucrose as filler and sweetener, artificial or natural flavors such as fruit or vanilla or chocolate flavoring, plus silicon dioxide and/or magnesium stearate as a physical binder to facilitate mechanical handling during preparation and packaging.

Preferred embodiments of the invention include compositions and dietary supplements, as described above, prepared in a 'mucosal delivery format'; particularly as an oral dosage form that promotes absorption of the dietary supplement's components through the epithelial lining of the oral cavity. Further preferred embodiments are methods for promoting those beneficial effects in mammals described above, in which such oral dosage forms of these compositions and dietary supplements are administered. Examples of oral dosage forms that promote absorption of the dietary supplement's components within the oral cavity are those that encourage retention of the dose within the oral cavity for an extended period, or discourage swallowing of the dose. Dosage forms that are chewable or that are appropriate for sucking are examples; they may be additionally designed to encourage salivation. Such dosage forms include lozenges, particularly chewable lozenges, chewable tablets and chewable gums. The addition of natural or artificial flavoring also encourages retention of the dosage form within the mouth, particularly with children, so that there is greater transfer of the active components through the lining of the oral cavity and into the bloodstream and/or the lymphatic system. Such active components include the constituents of colostrum and the lactoferrin, as described above. The physical size and consistency of the dosage form may also be adapted to prevent premature swallowing of the delivered dose; 30 seconds to ten minutes is the recommended period for which the dose should remain in the mouth for effective absorption, with better effects being observed at the longer retention times. Larger chewable forms are appropriate for animals that would otherwise be likely to swallow such foodstuff with little mastication.

In the currently most preferred embodiment of the invention the composition comprises the following ingredients cold pressed into a chewable lozenge of hardness 14 to 44 Kp that is taken as a nutritional supplement one to five times per day: 150 mg to 200 mg bovine prime colostrum, 10 mg to 20 mg bovine lactoferrin, 5 mg modified citrus pectin, 1295 mg to 1945 mg dextrose, 7.5 mg to 12.0 mg citric acid, 4.5 to 15.0 mg natural and/or artificial flavor (to taste), 7.5 mg silicon dioxide, 7.5 mg magnesium stearate and dextrose to a total weight of 0.5 to 3.0 grams. The lozenge is chewed for 30 seconds to ten minutes to maximize absorption of the active ingredients through the lining of the oral cavity and their absorption into the blood and lymphatic system.

2. Working Examples

In order to illustrate the nature of the invention more fully, and the manner in which it is to be practiced, the following examples are presented:

EXAMPLE 1

Product 'CLP': each of the following ingredients is placed, in powdered form, into a commercial mixer: 150 parts bovine prime colostrum, 10 parts bovine lactoferrin, 5 parts modified citrus pectin, 1297.5 parts dextrose, 7.5 parts citric acid, 15 parts natural strawberry flavor, 7.5 parts silicon dioxide and 7.5 parts magnesium stearate. If necessary the materials are passed through a # 10–12 mesh screen to remove aggregates. Each of the procedures should be performed with precautions against exposure to the powders and dusts that are formed, and particularly against their inhalation. After 20 minutes of thorough mixing cold pressing the composition in a tablet press set at a maximum pressure of 6.4 tons yielded lozenges of weight 1500 mg and hardness 34 to 36 Kp.

EXAMPLE 2

Product 'IGF 2020': each of the following ingredients is placed, in powdered form, into a commercial mixer following the same procedure as for Example 1: 200 parts bovine prime colostrum, 20 parts bovine lactoferrin, 5 parts modified citrus pectin, 1943.5 parts dextrose, 12 parts citric acid, 3 parts natural strawberry flavor, 1.5 parts artificial flavor (e.g. vanilla, chocolate) 7.5 parts silicon dioxide and 7.5 parts magnesium stearate. After mixing and cold pressing as in Example 1, lozenges of weight 2200 mg were formed which demonstrated a hardness of 34 to 36 Kp.

EXAMPLE 3

Product 'IGF 2020-J': each of the following ingredients is placed, in powdered form, into a commercial mixer following the same procedure as for Example 1: 200 parts bovine prime colostrum, 20 parts bovine lactoferrin, 5 parts modified citrus pectin, approximately 215 parts dextrose and/or maltodextrin, approximately 10 parts stearic acid as binder. After mixing and cold pressing as in Example 1, lozenges of total weight 400 mg to 600 mg were formed.

EXAMPLE 4

Product 'CLP' (Example 1) was self-administered by subject A, an adult woman with a long history of gastrointestinal disorders, including irritable bowel syndrome. Over several years subject A had experienced no relief from medications prescribed by physicians. Colon symptoms improved as soon as a regime was initiated in which four to five lozenges of product 'CLP' (Example 1) were dissolved slowly in the mouth daily. Over three months the irritable bowel syndrome improved to the point at which symptoms were absent.

EXAMPLE 5

Product 'CLP' (Example 1) was self-administered by Subject B, an adult man with a history of medical disorders following exposure to toxic defoliants. The subject has suffered from pancreatic failure and had been insulin dependent as a 'brittle diabetic' for twenty years, losing the sight in one eye during this time. After two months under a regime of two lozenges of product 'CLP' daily, the subject was able to halve his daily dosage of insulin, while observing over the same period improved healing of bruises and cuts, elimination of the splitting of fingernails and toenails, and noting an accompanying increase in energy level and alertness.

EXAMPLE 6

Product 'CLP' (Example 1) was self-administered by subject C, an adult male. At age 42, after an eighteen-month regime averaging three lozenges per day the subject's concentration of IGF-I (insulin-like growth factor-I) in the bloodstream was 393 ng ml$^{-1}$. This value is 175% of the median of the normal range for males of 40 to 54 years of age (90 to 360 ng ml$^{-1}$) and 9.2% higher than the upper limit of this range.

Clinical methods to measure IGF-I blood concentration are well known. In muscle IGF-I has several metabolic effects including the stimulation of glucose metabolism, increased uptake of nutrients, enhancement of cell proliferation and inhibition of protein degradation (Dohm et al., 1990, *Diabetes,* 39: 1028–1030; Tollefsen et al., 1989, *J. Biol. Chem.,* 264: 13810–13817). Thus levels of IGF-I in the blood indicate metabolic potential for healing and growth, which may reflect immune system activity. While the concentration of IGF-I circulating within the blood lies within a broad range for a population of subjects, a small variation in the concentration in a particular individual's blood can indicate a significant change in immunological stimulation. Thus the observation is indicative of a long-term beneficial effect of the dietary supplement of the invention.

EXAMPLE 7

Product 'IGF 2020' (Example 2) was self-administered by subject D, an adult male aged 30 years. Over a seven day regime of one lozenge per day the concentration of IGF-I in the blood of subject D rose 9.1%, from 265 ng ml$^{-1}$ to 289 ng ml$^{-1}$. This indicates a short-term beneficial effect of the dietary supplement of the invention.

EXAMPLE 8

Product 'CLP' (Example 1) was administered daily to Subject E, an elderly canine exhibiting, among other symptoms, intestinal bleeding. Contrary to the veterinary prognosis of rapid deterioration and death within days or weeks, evidence of the bleeding has ceased and Subject E has continued to survive for longer than six months.

It should be understood that the foregoing disclosure emphasizes certain specific embodiments of the invention and that all modifications or alternatives equivalent thereto are within the spirit and scope of the invention as set forth in the appended claims.

What is claimed is:

1. A dietary composition prepared as a lozenge, a chewable lozenge, or a chewable tablet, the composition comprising colostrum and modified citrus pectin.

2. The composition of claim 1, wherein the colostrum is present at a concentration of about 125 mg to about 1250 mg per 1500 mg total weight of the composition.

3. The composition of claim 1, wherein the pectin is present at a concentration of about 1.5 mg to about 15 mg per 1500 mg total weight of the composition.

4. The composition of claim 1, further comprising citric acid.

5. The composition of claim 1, further comprising one or more sweeteners, flavorings, carriers, diluents, or physical binders.

* * * * *